(12) United States Patent  
Genovesi

(10) Patent No.: US 8,162,815 B2  
(45) Date of Patent: Apr. 24, 2012

(54) METHOD AND DEVICE FOR PRESERVING THE VITALITY AND FUNCTION OF A HARVESTED BLOOD VESSEL

(76) Inventor: Mark Genovesi, New York, NY (US)

( * ) Notice: Subject to any disclaimer, the term of this patent is extended or adjusted under 35 U.S.C. 154(b) by 1224 days.

(21) Appl. No.: 11/653,528

(22) Filed: Jan. 16, 2007

(65) Prior Publication Data

US 2008/0169214 A1    Jul. 17, 2008

(51) Int. Cl.
*A01N 1/02*   (2006.01)
*A61F 2/06*   (2006.01)

(52) U.S. Cl. .................... 600/36; 435/1.2; 435/284.1

(58) Field of Classification Search ............ 600/36; 206/438; 435/283.1–309.4, 1.2; *A61F 2/06, A61F 2/00*
See application file for complete search history.

(56) References Cited

U.S. PATENT DOCUMENTS

| | | | |
|---|---|---|---|
| 4,417,861 A * | 11/1983 | Tolbert | 417/315 |
| 4,539,716 A * | 9/1985 | Bell | 600/36 |
| 5,035,708 A * | 7/1991 | Alchas et al. | 623/1.45 |
| 5,643,712 A | 7/1997 | Brasile | |
| 5,792,603 A * | 8/1998 | Dunkelman et al. | 435/1.2 |
| 5,919,170 A * | 7/1999 | Woessner | 604/264 |
| 6,416,995 B1 * | 7/2002 | Wolfinbarger | 435/289.1 |
| 6,818,003 B2 | 11/2004 | Genovesi | |
| 6,900,008 B2 | 5/2005 | Vinten-Johansem | |
| 2003/0069541 A1 * | 4/2003 | Gillis et al. | 604/164.01 |
| 2003/0097040 A1 * | 5/2003 | Clerin et al. | 600/36 |
| 2008/0208310 A1 * | 8/2008 | McDermott et al. | 623/1.11 |
| 2009/0104640 A1 * | 4/2009 | Barron et al. | 435/29 |

* cited by examiner

*Primary Examiner* — Charles A Marmor, II
*Assistant Examiner* — Catherine E Burk
(74) *Attorney, Agent, or Firm* — Richard L. Strauss, Esq.

(57) ABSTRACT

A blood vessel preservation device is disclosed comprised of a vessel cannister, cannister cap, vessel alignment insert, pulsatile pump and both inlet and outlet tubing. The vessel canister is advantageously configured as a hollow tube-like structure with a central bore having one open terminus—the proximal terminus—and a closed distal terminus—similar to a large test tube—. Integrated embodiments of the device are disclosed wherein blood is provided from natural circulation and returns thereto. Non-integrated embodiments are also disclosed wherein sufficient blood is provided to the device and thereafter the device functions separate and apart from a patient's circulatory system.

21 Claims, 4 Drawing Sheets

METHOD AND DEVICE FOR PRESERVING THE VITALITY AND FUNCTION OF A HARVESTED BLOOD VESSEL

TECHNICAL FIELD

The technology disclosed and claimed herein is most closely related to the science of blood vessel harvesting, preservation and grafting. More specifically, disclosed herein is a device and method for preserving an artery or vein, harvested for grafting, in a viable and functional state.

BACKGROUND OF THE INVENTION

Endothelial health and endothelial damage are major concerns in regard to coronary bypass grafts. This is especially true in regard to the late patency of such grafted vessels. To date, saline has been frequently utilized as preservative fluid for harvested vessels intended for use in bypass surgery. However, it is well known that saline produces significant endothelial damage in such vessels. It follows, as has been noted in various studies, that saline preserved grafts suffer significant impairment of vessel structure and function after anastomosis. In part, such degradation can be related to the absence of blood constituents which, in combination with natural blood flow, are required to maintain endothelial health.

The endothelial lining of arterial walls produces what was once known as endothelium-derived relaxing factor (which has since been identified as nitric oxide). Nitric oxide is, in turn, required in order for acetylcholine to effect relaxation of arterial smooth muscle—and to avoid damaging vessel spasms/contractions often noted in excised grafts. NO, derived from the endothelium has further vessel patency functions beyond muscle relaxation. It is known to protect the vessel by inhibiting platelet and neutrophil adhesion to the endothelial walls as well as the arrest of smooth muscle cell proliferation. Based on the two aforementioned functions of NO, it follows that, in regard to maintaining patency of grafted vessels, preservation of the endothelium's natural production and release of NO is of extreme importance.

While, as discussed above, it is known that saline is a rather poor solution for use in preserving arterial grafts, blood is an excellent preservative. However, due to the fact that the normal constituents of blood (platelets, fibrin, leukocytes) as well as plasma components (such as cholesterol and triglycerides), negatively interact and damage endothelium during the harvesting/handling procedures, the simple infusion of blood into a harvested vessel would, of course, include additional draw backs. These interactions, of course, constitute an additional concern in regard to vessel patency. The aforementioned interactions of blood and plasma constituents with the endothelial lining are exacerbated in regard to blood which is allowed to pool. However, blood flowing through a vessel, as it does in its natural, pre-excised demonstrates greatly diminished interactions between the above-described blood/plasma constituents and the endothelial wall. More specifically, there is a substantially higher degree of interaction between blood/plasma components and the endothelial lining of vessels in stagnant blood, allowed to simply pool in an excised vessel, as opposed to the degree of interaction found in vessels conducting pulsatile, flowing blood.

In regard to blood flow and its effect upon harvested vessels beyond the aforementioned constituent/endothelial interactions, it is well known, that application of a pulsatile flow to preservative solutions will improve and help maintain vessel dilatation. Pulsatile solution flow is also known to improve, nitric oxide production and release. In addition, flow pulsatility is known to reduce harvested vessel spasm. More specifically, harvested vessels, "acclimated" or conditioned to pulsatility—prior to being placed into arterial circulation—have increased likelihood of maintaining post-graft viability.

In addition to preservative fluid composition and flow, the temperature of storage and/or preservative solutions utilized to maintain harvested vessel vitality is of great significance. More specifically, as fluid temperature decreases below normal body temperature, loss of endothelium increases. Fluid temperatures beyond normal body temperature can also be quite damaging. It would therefore seem that a superior preservative technique, especially useful for the preservation of harvested blood vessels, would include the use of solutions maintained at normal body temperature.

Harvested vessels are also highly susceptible to damage caused by exposure to improper pH. For example, the relative acidic nature of normal saline is known to have detrimental effects on the endothelium. Also, hypoxic conditions which effect harvested vessels removed from active circulation can also cause enough damage as to substantially reduce graft survival. In addition, maintaining the natural patency of the lumen of harvested vessels, once removed from circulation, constitutes a problem. While over distension of such vessel due to the application of excess fluid pressure is highly damaging the endothelium, prolonged collapse of the lumen, and the associated hemolysis and clotting which may be caused thereby must also be avoided.

Blood is a superior preserving solution (as compared to saline). However, to date, a method and device have not been disclosed wherein blood, utilized as a preservative for harvested vessels, might be effectively and efficiently directed through the lumen of harvested arteries and veins while, at the same time, maintaining a temperature close to that of normal body temperature and a flow mimicking the pulsatile flow and pressure ranges to which the vessel is normally exposed (pre-excision)

SUMMARY OF THE INVENTION

Now in accordance with the present invention, a blood vessel preservation device is disclosed, especially configured and adapted to preserve the viability of harvested blood vessels. The blood vessel preservation device of the present invention maintains and preserves the viability of harvested vessels for a period of time sufficient to allow anastomosis sites to be properly accessed and prepared prior to grafting of the harvested vessel into said site.

The blood vessel preservation device is comprised of a vessel cannister, cannister cap, vessel alignment insert, pulsatile pump and both inlet and outlet tubing. The vessel canister is advantageously configured as a hollow tube-like structure with a central bore having one open terminus—the proximal terminus—and a closed distal terminus—similar to a large test tube—. It may, for example, be advantageously fabricated from a medical grade glass. The canister may also be advantageously fabricated from a medical grade plastic polymer such as, for example, acetal, polysulfone, polyphenylsulfone, polythermide, UHMW, polycarbonate, acrylic, polypropylene, PTFE and antimicrobial filled polymers. It is highly advantageous to utilize a transparent polymer for fabrication of the canister so as to enable gross visual observation of a vessel contained therein as discussed in more detail, below.

The cannister cap may be described as including a top portion configured in a flattened circular shape with side wall portions extending therefrom. During application of the cannister cap to a vessel canister, it is the top portion of the cannister cap that actually occludes the proximal opening of the vessel cannister The side walls of the cap, extending at approximately 90 degrees from the top portion, circumferentially engage the vessel cannister—either on the outside surface or inside surface therein—adjacent the proximal terminus thereof so as to maintain the cap upon the cannister with a fluid tight seal. As mentioned above, the side wall portion of the cannister cap is advantageously shaped and configured so that the inner or outer surfaces thereof mate with and form a seal with the vessel cannister adjacent to the proximal terminus thereof.

The cannister cap includes a vessel engagement fitting as well as a canister outlet fitting. The cannister cap may, for example, be advantageously formed from a medical grade glass material. It may be further advantageous to fabricate the cannister cap from a medical grade polymer such as, for example, acetal, polysulfone, polyphenylsulfone, polythermide, UHMW, polycarbonate, acrylic, polypropylene, PTFE and antimicrobial filled polymers.

The vessel engagement fitting, in a first preferred embodiment of the present invention, is mounted, eccentrically, within the top portion of the cannister cap as a contiguous structure thereof. The engagement fitting includes an opening at both the proximal and distal terminus thereof. The openings of the proximal and distal terminus of the engagement fitting are in fluid communication with a central bore running, axially, along the full length of the engagement fitting so as to form a conduit. When the cannister cap is matingly engaged with the vessel canister at the proximal terminus of the cannister, the distal portion of the vessel engagement fitting is contained within the vessel container and, in preferred embodiments, is axially aligned with the center of the central bore of the cannister. The outer surface of the engagement fitting, adjacent to the distal terminus thereof, may advantageously include circumferential ribs so as to, as described in more detail below, enhance engagement of the proximal portions (lumen) of harvested vessels.

In the first preferred embodiment of the present invention, the proximal terminus of the vessel engagement fitting extends obliquely outward and eccentrically from the top surface of the cannister cap. The outer surface of the proximal portion of the vessel engagement fitting is especially sized and configured to enable engagement of a blood inlet tube, discussed in detail, below. In certain embodiments of the present invention, this outer surface may also include circumferential ribs so as to better engage and maintain surgical tubing attached thereupon.

When the canister cap is matingly engaged to the vessel container, the proximal terminus of the engagement fitting extends outside of the cannister/cap. The distal terminus of the engagement fitting lies within and, in preferred embodiments of the present invention, is aligned with the central axis of the central bore of the cannister. The central bore of the engagement fitting, running from the distal to proximal terminus thereof, and communicating with the openings located at both such termini thus provides a conduit—a fluid communication between the central bore of the vessel container and the, through the opening at the proximal terminus of the vessel engagement fitting outside of the cannister (and to any tubing attached to the proximal terminus of the fitting).

A cannister outlet fitting—which in preferred embodiments of the present invention may also formed as a contiguous part of the cannister cap—, includes a central bore, as well as proximal and distal terminus (both defining opening), is center mounted upon the top portion of the cannister cap. The distal terminus of the outlet fitting defines an opening which, in certain preferred embodiments of the present invention, is within and continuous with the inner surface of the top portion of the cannister cap in the center thereof. When the cannister cap is engaged to the distal portion of the cannister, then the distal opening of the outlet fitting is open to and in fluid communication with the central bore of the vessel cannister. The proximal terminus, as described above, includes an opening which is in fluid communication with the central bore of the outlet fitting. Thus, a conduit is formed which runs from the opening at the proximal terminus of the outlet fitting, through the central bore of the outlet fitting and through the opening located at the distal terminus thereof. Thus, the proximal opening of the outlet fitting is open and in fluid communication with the central bore of the vessel cannister when the cap has engaged the vessel cannister.

The vessel alignment insert may be described as including a disc-like portion located at the distal part thereof, and a tube-like portion extending proximally therefrom. The disc-like portion may be configured, for example, to demonstrate a diameter slightly less than that of the central bore of the cannister so that, as described below, the disc helps extend and align a harvested vessel when the vessel is infused with blood. In preferred embodiments of the present invention, the disc-like portion includes a plurality of perforations therein, at least one of which is aligned with a central bore penetrating the disc-like portion of the insert and thence running the length of the tube-like portion of the vessel alignment insert and communicating with the proximal opening located at the proximal terminus of the tube-like portion. In certain preferred embodiments of the present invention, the outer surface of the tube-like portion of the insert, adjacent to the proximal terminus thereof, is especially configured to include circumferential ribs so as to facilitate engagement of the lumen of harvested vessels proximal to the distal portions thereof. As mentioned above, the distal terminus of the tube-like portion of the vessel alignment insert includes an opening aligned with and continuous with the central bore of the tube-like portion which, in turn, is aligned with and continuous with the at least one of the perforations of the disc-like portion of the insert. Therefore, there is fluid communication running from the proximal portion of the tube like portion of the insert, through the central bore thereof, and through at least one perforation of the disc-like portion of the insert. Thus, blood flowing within the harvested vessel, as discussed below, is able to exit the vessel, via the proximal opening of the insert, through the bore, and out the at least one perforation leading to the central bore of the cannister. The vessel alignment insert may be advantageously fabricated from a medical grade glass. However, it is still further advantageous to fabricate the insert from a medical grade plastic polymer such as, for example, acetyl, polysulfone, polyphenylsulfone, polythermide, UHMW, polycarbonate, acrylic, polypropylene, PTFE and antimicrobial filled polymers. As stated in regard to the vessel cannister and cannister cap, it is advantageous that the vessel insert be fabricated from a transparent material.

The device of the present invention utilizes a pulsatile pump so as to provide a pulsatile flow of blood through a harvested vessel contained within the vessel cannister (as described in more detail, below. This pulsatile flow tends to enhance the viability of a harvested vessel contained within the device. Ventricular-type pneumatic or hydraulic pumps (e.g., Keele pump, Polystan pulsatile pump), modified roller pumps (e.g., Sarns and Stockert), and modified centrifugal pumps (e.g., Sarns) may be advantageously selected as pulsatile pumps for use in the device of the present invention. In addition, roller pumps, and especially pulsatile roller pumps may be utilized. Regardless of the pumps utilized, the flow of the pump is adjusted so as to provided a pulse pressure of from about 60 to 150 mmHg. Within this pressure range, sufficient pressure is provided so as to maintain an open and patent harvested vessel lumen without danger of the damage caused by over distension thereof. Thus, the device of the present invention requires either a pressure regulated pump (a pump including an integral and adjustable pressure regulator), a separate pressure control device, or the use of both a variable output (pressure) pump and pressure control device.

In certain preferred embodiments of the present invention, wherein said device is utilized—as described in detail, below—separate and apart from a patients circulatory system, the device may further advantageously includes a means of warming blood circulating therethrough. Blood warmers such as the "Fluido" device (Fluido b.v., The Surgical Company) are especially useful in that they combine both accurate temperature control and monitoring functions The method of the present invention provides a means of enhancing and prolonging the viability of a harvested vessel by means of utilizing the device of the present invention, described above. The device of the present invention is most advantageously utilized immediately after a harvested blood vessel has been removed from a patient. In practicing the method of the present invention, initially, the distal end of the harvested vein (or artery) is clamped off. Thereafter, blood is forced into the lumen of the vessel at the proximal (and open) end of the vessel via manual syringe instillation. Manual infusion of blood into the harvested vessel is performed in order to identify any side branches not already tied off or clamped during the harvesting procedure. Any such side branches so identified (via the extravasation of blood) are quickly tide off, clamped or otherwise occluded in the usual manner.

Once the harvested vessel has been tested for side branches—and any identified side branches occluded—, the aforementioned clamp and syringe are removed therefrom. Thereafter, the proximal end of the tube-like portion of the vessel alignment insert is inserted into the lumen of the harvested vessel at the distal end of said vessel. The distal terminus of the vessel engagement fitting is then inserted with the lumen of the harvested vessel at the proximal terminus of said vessel. Thereafter, the vessel alignment insert is inserted into the bore of the vessel cannister, with the disc-like portion of the alignment insert being introduced first. Thereafter, the harvested vessel is introduced into the cannister and the cannister cap, now engaging the lumen of the harvested graft (adjacent the proximal terminus), is mated and engages the canister adjacent to the open proximal terminus thereof.

The device of the present invention is advantageously operated with—in preferred embodiments—, blood circulating from and returning to the patient undergoing the harvesting/graft procedure. The patients own naturally heated and oxygenated blood therefore serves as the preserving fluid for the harvested vessel. Therefore, for example, a catheter inserted into the patient's femoral artery may be utilized to supply blood, via the usual surgical tubing, to the inflow side of a pusatile pump used in accordance with the device and method of the present invention. The pulsatile pump, as discussed above, maintains natural flow pulsatility which, in turn, provides improved harvested vessel dilatation, nitric oxide production and reduction in vessel spasm. Thereafter, additional surgical tubing is utilized to connect the outflow of the pulsatile pump to the proximal end of the vessel engagement fitting. As discussed above, the opening at said proximal end of the vessel engagement fitting is in fluid connection with the central bore running the entire length of the engagement fitting, the opening at the distal end of the fitting and, of course, with the lumen of the harvested vessel now engaged by the fitting. Blood flowing from, for example, the femoral artery, thus travels through the surgical tubing to the pulsatile pump, and thence via further tubing through the vessel engagement fitting and on through the harvested vessel to the distal terminus thereof. Thereafter, blood passes through the opening located at the proximal end of the vessel alignment fitting, through the bore thereof and out the at least one perforation located on the disc-like portion of the fitting aligned with said bore. As the blood fills the vessel contained within the cannister, the pressure caused thereby, in conjunction with the vessel insert, causes the vessel to extend along the length of the vessel cannister to its full length. Thereafter, the blood fills the remaining central bore of the canister until it reaches the cannister outflow fitting located within the cannister cap. Blood which has filled the cannister and reached the outflow fitting thence passes through the opening located at the distal end of the fitting, passes through the bore thereof, and out the proximal opening of the fitting. Additional surgical tube, connecting the outflow fitting of the cannister cap, is utilized to provide return of blood circulated through the device and vessel maintained therein to a vein within the patient's circulation. As mentioned above, either a pressure regulator, integral to the pump utilized, or a separate pressure regulator, is utilized to maintain pressure entering the harvested vessel from about 50 to about 150 mmHG.

The above-described embodiment of the present invention may be described as an integrated blood flow embodiment of the method of the present invention. However, the present invention also contemplates embodiments thereof, wherein, after sufficient blood has been collected from the patient's circulation (as described above, the blood is continually circulated within the flow circuits of the device without return to the patient's own circulatory system. Such embodiments may also advantageously utilize a blood heating device so as to maintain the temperature of the blood substantially equal to normal body temperature. The above-described integrated embodiments wherein blood continuously flows from patient to device (and harvested vessel) and back to the patient obtain the heat required to maintain blood flowing through the harvested vessel at near normal body temperature from the patient's own body. However, non-integrated embodiments of the present invention which do not remain connected to a patient's circulation after initial "filling" of the system will continuously lose heat without the aforementioned additional heating device. These devices enable maintenance of blood temperature at about 40° C. and, of course, have overheat controls preventing blood from heating beyond 43° C. Blood warmers such as the "Fluido" device (Fluido b.v., The Surgical Company) are especially useful in that they combine both accurate temperature control and monitoring functions. In addition, such non-integrated embodiments may also utilize a reservoir in order to collect sufficient blood from a patient and thereafter make sufficient blood available for circulation through the vessel.

DETAILED DESCRIPTION

Figure 1:
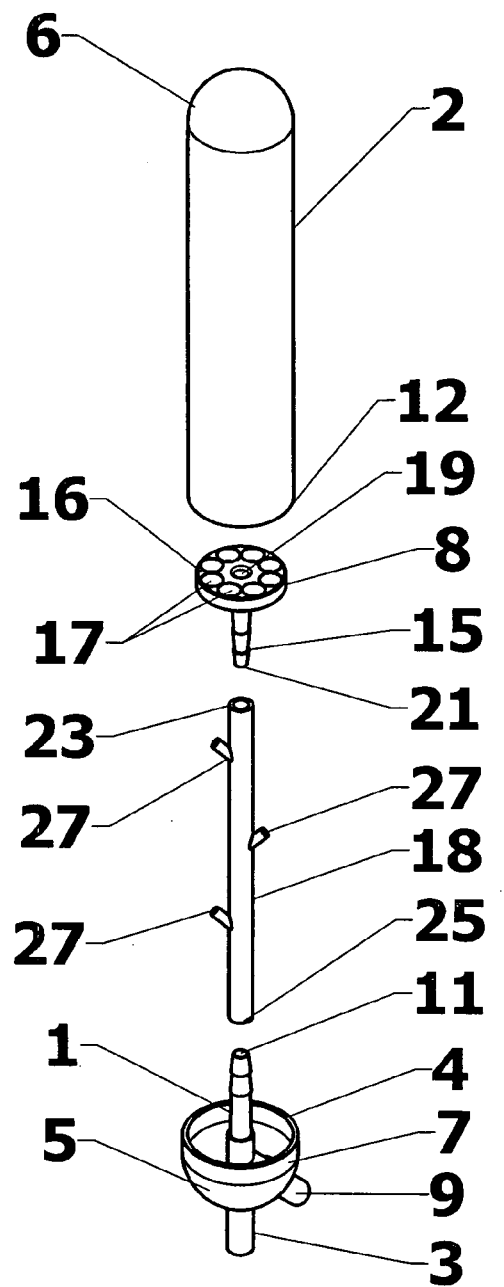
FIG. 1 illustrates an exploded view of a preferred vessel cannister, cannister cap and vessel alignment insert utilized in the device and method of the present invention.
Figure 2:
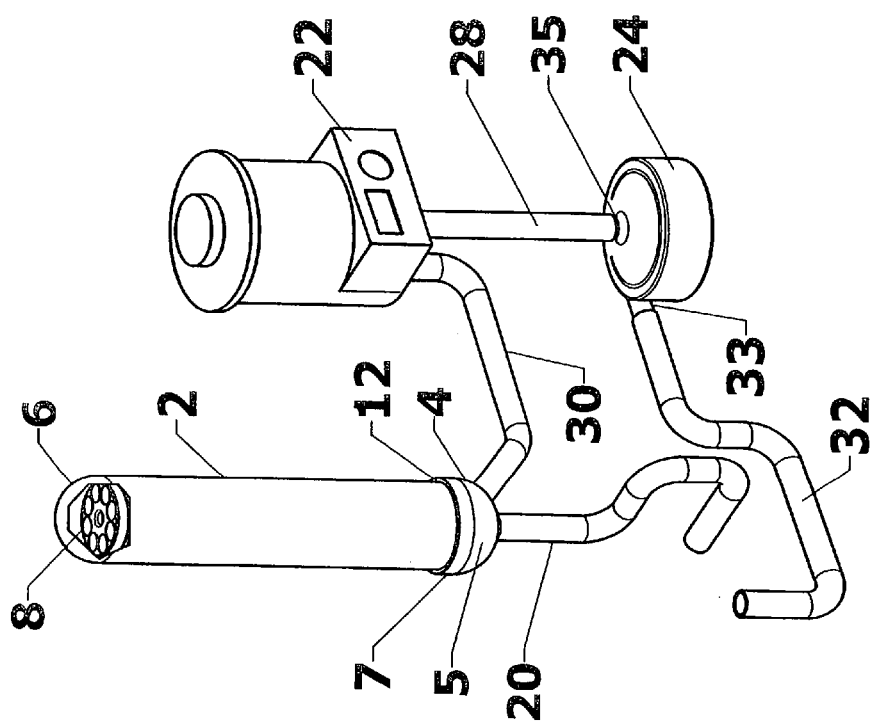
FIG. 2 is a front left view of the blood vessel preservation device of the present invention incorporating the vessel cannister, cannister cap and vessel alignment insert illustrated in FIG. 1.

As illustrated in FIG. 2, the blood vessel preservation device of the present invention is comprised of a vessel cannister 2, cannister cap 4, vessel alignment insert 8, pulsatile pump 24, and both inlet 30 outlet 20 tubing. As illustrated in FIG. 1, the vessel canister 2 is advantageously configured as a hollow tube-like structure with a central bore having one open terminus—the proximal terminus 12—and a closed distal terminus 6. The canister may be advantageously fabricated from a medical grade glass. The canister may also be advantageously fabricated from a medical grade plastic polymer such as, for example, acetal, polysulfone, polyphenylsulfone, polythermide, UHMW, polycarbonate, acrylic, polypropylene, PTFE and antimicrobial filled polymers. It is highly advantageous to utilize a transparent medical grade plastic for fabrication of the canister so as to enable gross visual observation of a vessel contained therein (as would, of course, also be provided by transparent, medical grade glass).

As illustrated in FIG. 1, the cannister cap 4 is comprised of a top portion 5 shaped and configured, for example, as a circular dome-like structure having side walls 7 extending therefrom. During application of the cannister cap to a vessel canister, it is the top portion of the cannister cap that actually occludes the proximal opening of the vessel cannister while the side walls of the cap, extending at approximately 90 degrees from the top portion, engage the vessel cannister circumferentially adjacent the proximal terminus thereof so as to maintain the cap upon the cannister with a fluid seal. The side wall portion of the cannister cap may be advantageously shaped and configured so that either the inner or outer surfaces thereof mate with and form a fluid seal with the vessel cannister adjacent to the proximal terminus of the cannister. The cannister cap includes a vessel engagement fitting 1 as well as a canister outlet fitting 3 which are described in more detail both above and below. The cannister cap may be advantageously formed of a medical grade glass material. It is further advantageous to fabricate the cannister cap from a medical grade polymer such as, for example, acetal, polysulfone, polyphenylsulfone, polythermide, UHMW, polycarbonate, acrylic, polypropylene, PTFE and antimicrobial filled polymers.

The cannister cap may be formed and configured so that the vessel engagement fitting 1, is mounted, for example, eccentrically, within the top portion of the cannister cap and as a contiguous structure thereof. The engagement fitting includes a central bore and has an opening at both the proximal 9 and distal 11 terminus thereof. The openings of the proximal and distal terminus of the engagement fitting are in fluid communication with the central bore running, axially, along the full length of the engagement fitting. When the cannister cap is matingly engaged with the vessel canister at the proximal terminus of the cannister, the distal portion of the vessel engagement fitting is contained within the vessel container and, in preferred embodiments of the present invention, is axially aligned with the center of the central bore of the cannister. The outer surface of the engagement fitting, adjacent to the distal terminus thereof, may advantageously include circumferential ribs so as to provide, as described in more detail below, enhanced engagement of the proximal portion (lumen) of harvested vessels. In preferred embodiments of the present invention (as illustrated in the figures), the proximal terminus of the vessel engagement fitting extends obliquely outward and eccentrically from the top surface of the cannister cap. The outer surface of the proximal portion of the vessel engagement fitting is especially sized and configured to enable engagement of a blood inlet tube, discussed in detail, below. In certain preferred embodiments of the present invention, the outer surface of the vessel engagement fitting, adjacent to the proximal terminus thereof, may also include circumferential ribs so as to better engage and maintain surgical tubing attached thereupon.

As discussed above, when the canister cap is matingly engaged about the proximal terminus of the vessel container, the proximal terminus of the engagement fitting extends obliquely outside of the cannister/cap and the distal terminus lies within and is aligned with the central axis of the central bore of the cannister. Thus, the central bore of the engagement fitting, running from the distal to proximal terminus thereof, and communicating with the openings located at both such termini, provides fluid communication between the central bore of the vessel container and the opening at the proximal terminus of the vessel engagement fitting (as well as any tubing attached thereto).

A cannister outlet fitting 3—in certain preferred embodiments as shown in the figures, is formed as a contiguous part of the cannister cap—. The cannister outlet fitting includes a central bore in fluid communication with openings formed at the proximal and distal terminus of the outlet fitting. In preferred embodiments of the present invention, it is preferred that the canister outlet fitting 3 be center mounted upon the top portion of the cannister cap. As mentioned above, the distal terminus of the outlet fitting defines an opening within and continuous with the inner surface of the top portion of the cannister cap in the center thereof. Thus, the distal opening of the outlet fitting is open to and continuous with the central bore of the outlet fitting which is also continuous, and provides fluid communication with the proximal opening thereof. Thus the proximal terminus of the outlet fitting is open and in fluid communication with the central bore of the vessel cannister when the cap has engaged upon the vessel cannister.

A vessel alignment insert 8 is provided having a distal disc-like portion 16 and a tube-like portion 15 extending proximally therefrom. The disc-like portion 16 of the insert demonstrates a diameter slightly less than that of the central bore of the cannister so that, as described in more detail below, when blood is pumped through a harvested vessel mounted upon the insert, the disc helps extend and align a harvested vessel within the central bore of the cannister. The disc-like portion includes a plurality of perforations therein 17, at least one of which, preferably a central perforation 19, is aligned with and in fluid communication with a central bore running the length of the tube-like portion 15 of the vessel alignment insert and thus communicates with a proximal opening located at the proximal terminus 21 of the tube-like portion. All of the afore-mentioned perforations are also in fluid communication with the central bore of the vessel cannister. An outer surface of the tube-like portion of the insert, adjacent to the proximal terminus thereof, may advantageously include circumferential ribs so as to facilitate engagement of the lumen of harvested vessels at the distal portions thereof. As mentioned above, the proximal 21 terminus of the tube-like portion of the vessel alignment insert includes an opening aligned with and continuous with the central bore of the tube-like portion which, in turn, is aligned with and continuous with the at least one of the perforations—preferably a centrally positioned perforation 19—of the disc-like portion 16 of the insert. Therefore, there is fluid communication running from the proximal portion of the tube like portion of the insert, through the central bore thereof, and through at least one perforation of the disc-like portion of the insert. Thus, blood flowing through the lumen of a harvested vessel mounted upon the insert, as discussed below, is able to exit the vessel, via the proximal opening of the insert, through the bore, and out the at least one perforation leading to the central bore of the cannister. The vessel alignment insert is advantageously fabricated from a medical grade glass. However, it is still further advantageous to fabricate the insert from a medical grade plastic polymer such as, for example, acetal, polysulfone, polyphenylsulfone, polythermide, UHMW, polycarbonate, acrylic, polypropylene, PTFE and antimicrobial filled polymers. As stated in regard to the vessel cannister and cannister cap, it is advantageous that the vessel insert be fabricated from a transparent material.

Figure 3:
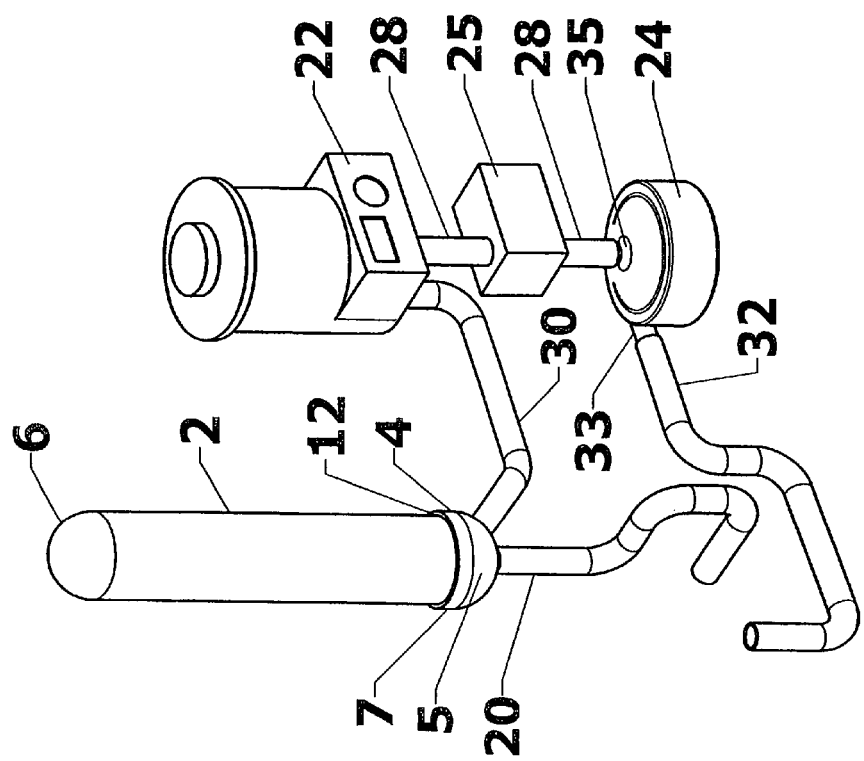
FIG. 3 is a front left view of a second preferred embodiment of the blood vessel preservation device of the present invention incorporating the vessel cannister, cannister cap and vessel alignment insert illustrated in FIG. 1.
Figure 4:
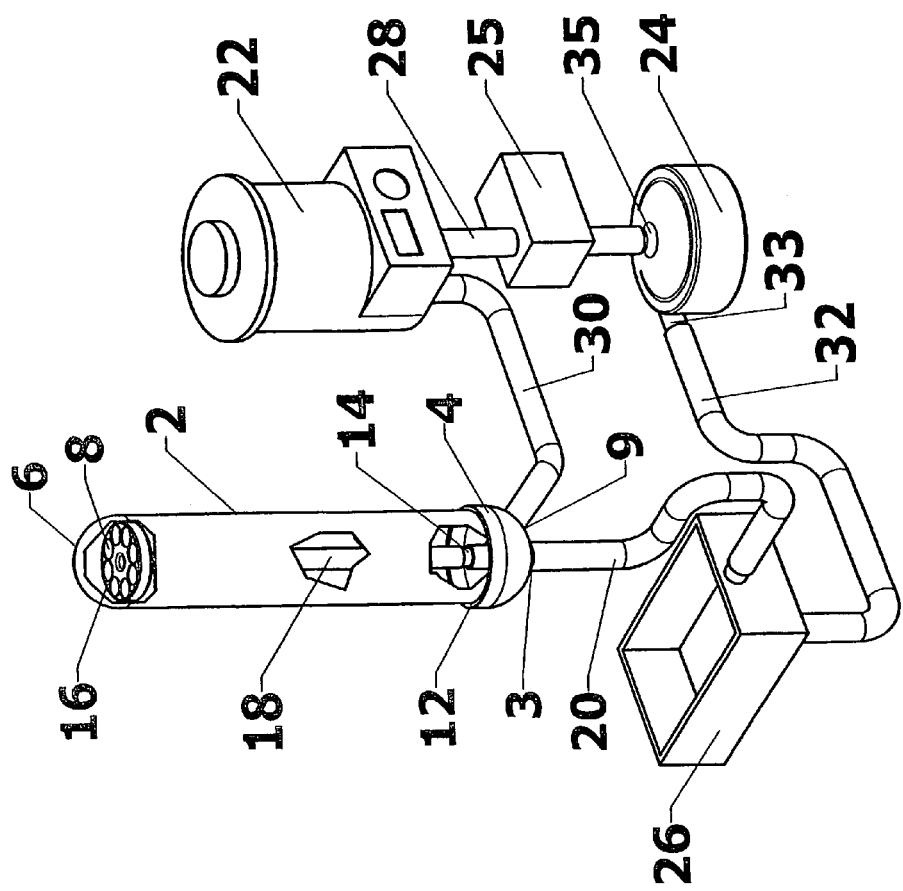
FIG. 4 is a front left view of a third preferred embodiment of the blood vessel preservation device of the present invention incorporating the vessel cannister, cannister cap and vessel alignment insert illustrated in FIG. 1.

As illustrated in FIGS. 2, 3 and 4, the device of the present invention utilizes a pulsatile pump 24 so as to provide a pulsatile flow of blood through a harvested vessel contained within the vessel cannister (as described in more detail, below). As described above, pulsatile blood flow tends to enhance the viability of a harvested vessels and thus also enhances the viability of vessels contained within the cannister through which pulsatile blood flow is provided. Ventricular-type pneumatic or hydraulic pumps (e.g., Keele pump, Polystan pulsatile pump), modified roller pumps (e.g., Sarns and Stockert), and modified centrifugal pumps (e.g., Sarns) may be advantageously selected as pulsatile pumps for use in the device of the present invention. In addition, roller pumps, and especially pulsatile roller pumps may be utilized. Regardless of the pumps utilized, the flow of the pump is adjusted so as to provided a pulse pressure of from about 60 to 150 mmHg. Within this pressure range, sufficient pressure is provided so as to maintain an open and patent harvested vessel lumen without danger of the damage caused by over distension thereof. To maintain pressure within this range, the device of the present invention requires either a pressure regulated pump (a pump including an integral and adjustable pressure regulator), a separate pressure control device 25 as illustrated in FIGS. 3 and 4, or the use of both a variable output (pressure) pump and pressure control device.

In certain preferred embodiments of the present invention, wherein said device is utilized—as described in detail, below—separate and apart from a patients circulatory system, the device further includes a means of warming blood circulating therethrough. Such devices are required since, as described above, harvested vessel viability is enhanced by providing blood temperature close to natural somatic levels. Blood warmers such as the "Fluido" device (Fluido b.v., The Surgical Company) are especially useful in that they combine both accurate temperature control and monitoring functions The method of the present invention provides a means of enhancing and prolonging the viability of a harvested vessel by means of utilizing the device of the present invention, described above so as to provide a pulsatile flow of blood, at the temperature and pressure ranges discussed above, through a harvested vessel.

The device of the present invention is most advantageously utilized immediately after a harvested blood vessel has been removed from a patient. In practicing the method of the present invention, initially, the distal end 23 of the harvested vein (or artery) 18 is clamped off. Thereafter, blood is infused into the lumen of the vessel at the proximal 25 (and open) end of the vessel via manual syringe instillation. Manual infusion of blood into the harvested vessel is performed in order to identify any side branches 27 not already tied off or clamped during the harvesting procedure. Any such side branches so identified (via the extravasation of blood) are quickly tide off, clamped or otherwise occluded.

Once the harvested vessel has been tested for side branches—and any identified side branches occluded—, the aforementioned clamp and syringe are removed therefrom. Thereafter, the proximal end 21 of the tube-like portion of the vessel alignment insert is inserted into the lumen of the harvested vessel at the distal end 23 of said vessel. The distal terminus 11 of the vessel engagement fitting is then inserted with the lumen of the harvested vessel at the proximal terminus 25 of said vessel. Thereafter, the vessel alignment insert is inserted into the bore of the vessel cannister, with the disc-like portion of the alignment insert being introduced first. Thereafter, the harvested vessel is introduced into the cannister and the cannister cap, now engaging the lumen of the harvested graft (adjacent the proximal terminus), is mated and engages the canister adjacent to the open proximal terminus thereof.

The device of the present invention is advantageously operated with—in preferred embodiments—, blood circulating from and returning to the patient undergoing the harvesting/graft procedure. The patients own naturally heated and oxygenated blood therefore serves as the preserving fluid for the harvested vessel. Therefore, for example, a catheter inserted into the patient's femoral artery may be utilized to supply blood, via the usual surgical tubing 32, to the inflow side 33 of a pusatile pump 24 used in accordance with the device and method of the present invention. The pulsatile pump, as discussed above, maintains natural flow pulsatility which, in turn, provides improved harvested vessel dilatation, nitric oxide production and reduction in vessel spasm. Thereafter, in certain preferred embodiments of the present invention, additional surgical tubing 28 is utilized to connect the outflow 35 of the pulsatile pump:

1. directly to the proximal end of the vessel engagement fitting 9;

2. to the input of a pressure regulation device 25 which, in turn, directs the blood, via its output side, directly to the vessel engagement fitting or, 3 in other preferred embodiments, directs blood flow to a blood warmer 22.

In embodiments of the present invention utilizing a blood warmer, outflow therefrom may be directed to the vessel engagement fitting.

As discussed above, the opening at the proximal end of the vessel engagement fitting is in fluid connection with the central bore running the entire length of the engagement fitting, the opening at the distal end of the fitting and, of course, with the lumen of the harvested vessel engaged by the fitting. Blood flowing from, for example, the femoral artery, thus travels through the surgical tubing to the pulsatile pump, and thence via further tubing 28 either directly to the vessel engagement fitting and on through the harvested vessel to the distal terminus thereof. (In other preferred embodiments of the invention discussed above and below, blood outflowing from the pulsatile pump may first pass through an intermediary pressure regulator and, in certain preferred embodiments, a blood warmer prior to being directed to and through the vessel engagement fitting.)

As described above, after blood has passed through the lumen of the harvested vessel, it is directed through the opening located at the proximal end of the vessel alignment fitting, through the bore thereof and out the at least one perforation located on the disc-like portion of the fitting aligned with said bore. Thereafter, the blood fills the central bore of the canister until it reaches the cannister outflow fitting located within the cannister cap. Blood which has reached the outflow fitting thence passes through the opening located at the distal end of the fitting, passes through the bore thereof, and out the proximal opening of the fitting. Additional surgical tube 20, connecting the outflow fitting of the cannister cap, is utilized to provide return of blood circulated through the device and vessel maintained therein to a vein within the patient's circulation. As mentioned above, either a pressure regulator, integral to the pump utilized, or a separate pressure regulator, is utilized to maintain pressure entering the harvested vessel from The above-described embodiment of the present invention may be described as an integrated blood flow embodiment of the method of the present invention.

The present invention also contemplates embodiments thereof, wherein, after sufficient blood has been collected from the patient's circulation (as described above, the blood is continually circulated within the flow circuits of the device without return to the patient's own circulatory system. Such embodiments—as illustrated in FIG. 4—may also advantageously utilize a reservoir 26 for containing sufficient blood for circulation as well as a blood heating device 22 so as to maintain the temperature of the blood substantially equal to normal body temperature. The above-described integrated embodiments wherein blood continuously flows from patient to device (and harvested vessel) and back to the patient may obtain the heat required to maintain blood flowing through the harvested vessel at near normal body temperature from the patient's own body. However, non-integrated embodiments of the present invention which do not remain connected to a patient's circulation after initial "filling" of the system will continuously lose heat without the aforementioned additional heating device. These devices enable maintenance of blood temperature at about 40° C. and, of course, have overheat controls preventing blood from heating beyond 43° C. Blood warmers such as the "Fluido" device (Fluido b.v., The Surgical Company) are especially useful in that they combine both accurate temperature control and monitoring functions.

The terms and expressions which have been employed in the foregoing specification and in the abstract are used therein as terms of description and not limitation, and there is no intention, in the use of such terms and expressions, of excluding equivalents of the features shown and described or portions thereof, it being recognized that the scope of the invention is defined and limited only by the following claims.

I claim:

1. A harvested blood vessel preservation device comprised of a blood vessel cannister, cannister cap, and blood vessel alignment insert, wherein
   the blood vessel cannister is shaped and configured as a hollow tube having a proximal terminus, distal terminus and central bore wherein an opening, continuous with said central bore is located at said proximal terminus only;
   the cannister cap includes a blood vessel engagement fitting and a cannister outlet fitting; and
   the blood vessel alignment insert is comprised of a tube-like portion and a disc-like portion, said disc-like portion configured and formed in the shape of a flattened disc having at least one perforation therethrough located at a center point of said disc-like portion the tube-like portion of the blood vessel alignment insert being especially configured and adapted to engage the distal end of a harvested vessel contained within the vessel cannister and the entire tube-like portion being located and positioned proximal to the disc-like portion, the at least one perforation at the center point of said disc-like portion being especially configured and positioned to provide fluid communication with the central bore of the canister, said tube-like portion having an opening at both proximal and distal termini thereof and a central bore therewithin running from said proximal to said distal termini, the distal terminus of said tube-like portion being continuous with and extending from the disc-like portion of the blood vessel alignment insert at said center point thereof, wherein a conduit is provided running from the opening at the proximal terminus of said tube-like portion, through the central bore thereof, through the opening at the distal terminus of said tube-like portion and thence through the at least one perforation of the disk-like member located at the center point thereof said conduit thereby enabling fluid, exiting the at least one perforation of the alignment insert to enter and fill the central bore of the canister, thereby wetting the outside surface of the blood vessel wherein when a pulsatile flow of blood, derived from a patient from whom a harvested vessel is removed, is passed through a harvested vessel contained within said blood vessel cannister, the harvested vessel contained therein is preserved in a viable state until it can be grafted back into the patients circulatory system at a desired and prepared location.

2. The device of claim 1 wherein said canister is fabricated from a medical grade glass.

3. The device of claim 1 wherein said canister is fabricated from a medical grade plastic polymer.

4. The device of claim 3 wherein said medical grade polymer is selected from the group consisting of acetal, polysulfone, polyphenylsulfone, polythermide, UHMW, polycarbonate, acrylic, polypropylene, PTFE and antimicrobial filled polymer.

5. The device of claim 4 wherein said medical grade polymer is transparent.

6. The device of claim 1 wherein said canister cap is fabricated from a medical grade glass.

7. The device of claim 1 wherein said canister cap is fabricated from a medical grade plastic polymer.

8. The device of claim 7 wherein said medical grade polymer is selected from the group consisting of acetal, polysulfone, polyphenylsulfone, polythermide, UHMW, polycarbonate, acrylic, polypropylene, PTFE and antimicrobial filled polymer.

9. The device of claim 8 wherein said medical grade polymer is transparent.

10. The device of claim 1 wherein said vessel alignment insert is fabricated from a medical grade glass.

11. The device of claim 1 wherein said medical alignment insert is fabricated from a medical grade plastic polymer.

12. The device of claim 11 wherein said medical grade polymer is selected from the group consisting of acetal, polysulfone, polyphenylsulfone, polythermide, UHMW, polycarbonate, acrylic, polypropylene, PTFE and antimicrobial filled polymer.

13. The device of claim 12 wherein said medical grade polymer is transparent.

14. The device of claim 1 wherein said pulsatile flow of blood is provided by a pulsatile pump connected to said cannister by means of surgical tubing and wherein said pump is selected from the group consisting of ventricular-type pneumatic, ventricular-type hydraulic, modified roller, and modified centrifugal pumps.

15. The device of claim 14 wherein said device further includes a means of adjusting output pressure of blood flowing from the pulsatile pump from about 50 to 150 mmHG of pressure.

16. The device of claim 1 wherein the disc-like portion of the blood vessel alignment insert includes a plurality of perforations therethrough.

17. The device of claim 1 wherein the canister cap includes a top portion and a side wall portion and wherein the blood vessel engagement fitting and a cannister outlet fitting is positioned and mounted within said top portion of the cannister cap.

18. A harvested blood vessel preservation device comprised of a blood vessel cannister, cannister cap, a blood vessel alignment insert, a pulsatile pump and surgical tubing wherein
  the blood vessel cannister is shaped and configured as a hollow tube having a proximal terminus, distal terminus and wherein said canister includes a central bore having a diameter and a length wherein an opening, continuous with said central bore is located at said proximal terminus only;
  the cannister cap includes a top portion and a side wall portion wherein a blood vessel engagement fitting and a cannister outlet fitting is positioned and mounted within said top portion of the cannister cap; and
  the blood vessel alignment insert is comprised of a tube-like portion and a disc-like portion, said disc-like portion configured and formed in the shape of a flattened disc demonstrating a diameter less than the diameter of the central bore of the cannister thereby enabling the alignment insert to move along the length of the bore, said disc-like portion also having a plurality of perforations therethrough, at least one of the perforations being located at a center point of said disc-like portion, the tube-like portion of the blood vessel alignment insert being especially configured and adapted to engage the distal end of a harvested vessel contained within the vessel cannister and the entire tube-like portion being located and positioned proximal to the disc-like portion of the tube-like portion, the at least one perforation at the center point of said disc-like portion being especially configured and positioned to provide fluid communication with the central bore of the canister, said tube-like portion having an opening at both proximal and distal termini thereof and a central bore therewithin running from said proximal to said distal termini, the distal terminus of said tube-like portion being continuous with and extending from the disc-like portion of the blood vessel alignment insert at said center point thereof, wherein a conduit is provided running from the opening at the proximal terminus of said tube-like portion, through the central bore thereof, through the opening at the distal terminus of said tube-like portion through the at least one perforation of the disk-like member located at the center point thereof and to the central bore of the vessel cannister;
  wherein when a blood vessel harvested from a patient is contained within said cannister and blood is pumped therethrough by means of the pulsatile pump, the vessel contained therein is preserved in a viable state until it can be grafted back into the patients circulatory system at a desired and prepared location.

19. The device of claim 18 wherein said pulsatile pump is selected from the group consisting of ventricular-type pneumatic, ventricular-type hydraulic, modified roller, and modified centrifugal pumps.

20. The device of claim 19 wherein said device further includes a means of adjusting output pressure of blood flowing from the pulsatile pump from about 50 to 150 mmHG of pressure.

21. The device of claim 18 wherein said device further comprises a blood warmer.

* * * * *